(12) United States Patent
Dib et al.

(10) Patent No.: US 10,058,675 B2
(45) Date of Patent: *Aug. 28, 2018

(54) INFUSION CATHETER TIP FOR BIOLOGICS WITH REINFORCED EXTERNAL BALLOON VALVE

(71) Applicant: Cook Regentec LLC, Indianapolis, IN (US)

(72) Inventors: Nabil Dib, Paradise Valley, AZ (US); Robert Edward Kohler, Lake Elmo, MN (US)

(73) Assignee: Cook Regentec LLC, Indianapolis, IN (US)

(*) Notice: Subject to any disclaimer, the term of this patent is extended or adjusted under 35 U.S.C. 154(b) by 878 days.

This patent is subject to a terminal disclaimer.

(21) Appl. No.: 14/145,158

(22) Filed: Dec. 31, 2013

(65) Prior Publication Data
US 2014/0114239 A1    Apr. 24, 2014

Related U.S. Application Data

(63) Continuation-in-part of application No. 13/473,988, filed on May 17, 2012, now Pat. No. 8,790,298, (Continued)

(51) Int. Cl.
*A61M 25/00* (2006.01)
*A61M 25/10* (2013.01)
(Continued)

(52) U.S. Cl.
CPC .... *A61M 25/0023* (2013.01); *A61M 25/0071* (2013.01); *A61M 25/0075* (2013.01);
(Continued)

(58) Field of Classification Search
CPC ........ A61M 25/0023; A61M 25/10184; A61M 25/10181; A61M 25/0071;
(Continued)

(56) References Cited

U.S. PATENT DOCUMENTS

| 4,465,481 A | 8/1984 | Blake |
| 4,608,984 A | 9/1986 | Fogarty |

(Continued)

FOREIGN PATENT DOCUMENTS

| EP | 0 318 918 A2 | 6/1989 |
| EP | 2 389 973 A1 | 11/2011 |

(Continued)

OTHER PUBLICATIONS

JP 2009-522010 A, English Abstract.
(Continued)

*Primary Examiner* — Theodore Stigell
(74) *Attorney, Agent, or Firm* — Woodard, Emhardt, Moriarty, McNett & Henry LLP

(57) ABSTRACT

A system for moving particles suspended in a first fluid, and for infusing them into the stream of a second fluid, includes a catheter with a multi-lumen distal separator. The separator is formed with a plurality of parallel lumens, wherein each lumen has a predetermined diameter to reduce particle flocculation. An inflatable balloon, affixed to the outside of the catheter, can be provided to regulate flow of the second fluid and thereby facilitate entry of the particles into the stream of the second fluid. A reinforcing member is employed to strengthen the catheter wall under the inflatable balloon. With this arrangement, the catheter does not kink or collapse due to the pressure exerted on the catheter wall when the balloon is inflated. In one embodiment, the reinforcing member includes an annular shaped ring. In another embodiment, the separator is positioned under the balloon and acts as the reinforcing member.

29 Claims, 6 Drawing Sheets

Related U.S. Application Data which is a continuation-in-part of application No. 12/563,876, filed on Sep. 21, 2009, now Pat. No. 8,647,311.

(51) Int. Cl.
  *A61M 39/10* (2006.01)
  *A61M 25/01* (2006.01)
  *A61M 39/08* (2006.01)

(52) U.S. Cl.
  CPC ......... *A61M 25/10* (2013.01); *A61M 25/1002* (2013.01); *A61M 39/105* (2013.01); *A61M 2025/0073* (2013.01); *A61M 2025/0183* (2013.01); *A61M 2025/1097* (2013.01); *A61M 2039/085* (2013.01); *A61M 2205/3334* (2013.01); *A61M 2206/18* (2013.01)

(58) Field of Classification Search
  CPC .......... A61M 25/0075; A61M 25/1002; A61M 2025/0183; A61M 2025/1097; A61M 2205/3334; A61M 2206/18; A61M 2025/0073; A61M 39/105; A61M 2039/085; A61M 25/005; A61M 2025/0059; A61M 25/10
  USPC ....................... 604/96.01, 523–527
  See application file for complete search history.

(56) References Cited

U.S. PATENT DOCUMENTS

| | | | |
|---|---|---|---|
| 5,000,734 A * | 3/1991 | Boussignac | A61M 25/10 604/103.06 |
| 5,156,594 A | 10/1992 | Keith | |
| 5,354,279 A | 10/1994 | Hofling | |
| 5,447,497 A | 9/1995 | Sogard et al. | |
| 5,447,797 A | 9/1995 | Sogard et al. | |
| 5,913,842 A | 6/1999 | Boyd et al. | |
| 5,964,223 A | 10/1999 | Baran | |
| 6,048,332 A | 4/2000 | Duffy et al. | |
| 6,312,374 B1 | 11/2001 | von Hoffmann | |
| 6,319,248 B1 | 11/2001 | Nahon | |
| 6,394,978 B1 | 5/2002 | Boyle | |
| 6,524,302 B2 | 2/2003 | Kelley | |
| 6,579,287 B2 | 6/2003 | Wittenberger et al. | |
| 6,840,920 B2 | 1/2005 | Millerd | |
| 8,647,311 B2 | 2/2014 | Dib | |
| 8,790,298 B2 | 7/2014 | Dib | |
| 2002/0188276 A1* | 12/2002 | Evans | A61B 17/22 604/509 |
| 2003/0130610 A1 | 7/2003 | Mager et al. | |
| 2003/0204171 A1 | 10/2003 | Kucharczyk et al. | |
| 2005/0226855 A1 | 10/2005 | Alt et al. | |
| 2005/0287125 A1 | 12/2005 | Morris et al. | |
| 2006/0004316 A1 | 1/2006 | Difiore et al. | |
| 2006/0030814 A1 | 2/2006 | Valencia et al. | |
| 2007/0106208 A1* | 5/2007 | Uber, III | A61M 5/142 604/65 |
| 2008/0039786 A1 | 2/2008 | Epstein et al. | |
| 2009/0157042 A1 | 6/2009 | Cheng et al. | |
| 2010/0004593 A1 | 1/2010 | Gregorich | |
| 2010/0210927 A1 | 8/2010 | Gillies et al. | |
| 2010/0234804 A1 | 9/2010 | Hiejima et al. | |
| 2011/0071496 A1 | 3/2011 | Dib | |
| 2011/0295114 A1 | 12/2011 | Renovorx | |
| 2012/0035595 A1* | 2/2012 | Goedje | A61B 5/205 604/544 |
| 2012/0041359 A1 | 2/2012 | Schoenle et al. | |
| 2012/0148668 A1 | 6/2012 | Consigny et al. | |
| 2012/0226225 A1 | 9/2012 | Dib | |
| 2012/0245521 A1 | 9/2012 | Gulachenski et al. | |
| 2014/0114239 A1 | 4/2014 | Dib et al. | |
| 2014/0207107 A1 | 7/2014 | Dib et al. | |

FOREIGN PATENT DOCUMENTS

| | | |
|---|---|---|
| JP | H08-38607 A | 2/1996 |
| JP | H11-504233 | 4/1996 |
| JP | 2002-543868 | 12/2002 |
| JP | 2009-522010 A | 6/2009 |
| WO | WO 1999/025421 A1 | 5/1999 |
| WO | WO 00/67647 | 11/2000 |
| WO | WO 2008/020967 | 2/2008 |
| WO | 2008057370 A2 | 5/2008 |
| WO | WO 2013/173166 A1 | 11/2013 |
| WO | WO 2015/102820 A2 | 7/2015 |

OTHER PUBLICATIONS

Translation of Office Action dated Apr. 28, 2015 in related JP Application No. 2012-529945.
WO2007079152 (A2) English Abstract related to JP 2009522010 (A).
PCT International Search Report, Application No. PCT/US2014/069253, dated Dec. 9, 2014.
Written Opinion issued for Application No. 11201407429P dated Aug. 28, 2015.
JP H11-504233 A, English Abstract.
English Abstract of JP H08-38607 A.

* cited by examiner

INFUSION CATHETER TIP FOR BIOLOGICS WITH REINFORCED EXTERNAL BALLOON VALVE

This application is a continuation-in-part of application Ser. No. 13/473,988 filed May 17, 2012, now U.S. Pat. No. 8,790,298 which is a continuation-in-part of application Ser. No. 12/563,876, filed Sep. 21, 2009, now U.S. Pat. No. 8,647,311. The contents of application Ser. No. 13/473,988 and application Ser. No. 12/563,876 are both incorporated by reference herein.

FIELD OF THE INVENTION

The present invention pertains generally to infusion systems for introducing particles into a fluid stream. More particularly, the present invention pertains to infusion systems for introducing (infusing) particles of biological matter (e.g. stem cells) into the vasculature of a patient without diminishing the therapeutic effectiveness of the biological matter. The present invention is particularly, but not exclusively, useful as a system using a multi-lumen filter that allows particles to enter a lumen of the separator, either individually or in small groupings, for subsequent infusion into the vasculature of a patient.

BACKGROUND OF THE INVENTION

An introduction of particles into the vasculature of a patient requires simultaneously satisfying several different concerns or considerations. Depending on the type of particles involved, a concern of significant importance involves preventing the particles from flocculating, i.e. clumping together, as they are being infused or introduced into the vasculature. This is of particular concern in the case of stem cells which can flocculate, but which are most effective in therapy if left to function either as individual cells or in small groups of cells. An additional benefit of preventing particles from flocculating is the prevention of heart attacks caused when clumps of cells are introduced into the coronary circulatory system. Also, it is possible that the retention rate of stem cells in the heart, or other targeted tissue, will increase when the stem cells are infused while flow is slow when the valve or the balloon might help in reducing blood flow.

In all types of intravascular therapy (i.e. intracoronary, intra-arterial or intravenous), it is always an essential concern that the therapeutic agent (e.g. biologics or drugs) be infused or delivered in a predictably controlled manner. Furthermore, it is important that the therapeutic agent be effectively delivered to a proper destination in the vasculature. All of this involves dosage and delivery rate considerations. Moreover, it requires careful handling of the therapeutic agent to insure it (the therapeutic agent) is not damaged or otherwise compromised during an infusion.

From a mechanical perspective, it is known that the diameter of a fluid passageway is a factor that will affect the rate of fluid flow through the passageway. For protocols where small groups of de-flocculated particles are to be infused into a vessel of a vasculature, the diameter of the passageway must obviously be large enough to individually accommodate the small groups of particles. On the other hand, it must also be small enough to separate and prevent larger groups of particles (cells) from clinging to each other. A consequence of this is that the rate at which particles can be carried through the passageway will be circumscribed by the dimensions of the passageway. A further consequence of this is that, as particles leave the passageway, they are then influenced by the flow of fluid (i.e. blood) in the vessel of the vasculature. Depending on the purpose of the protocol, this may mean that the downstream fluid flow in the vasculature will somehow also need to be regulated.

In some cases, the downstream fluid flow in the vasculature (discussed above) can be controlled or regulated using an inflatable balloon that is attached to an outside surface of the catheter tube. For these and similar arrangements, when the balloon is deployed at the treatment site (i.e. inflated), a pressure is exerted on the catheter tube. The catheter tube, however, is typically made of a flexible material to allow it to twist and turn as the catheter is navigated through the patient's vasculature. Because of the flexible nature of the catheter tube, it is typically susceptible to kinking and/or collapse during inflation of the balloon. This can be particularly troublesome for infusion catheters where the material to be infused is pumped through a central lumen of the catheter tube. In this instance, a collapse or even partial blocking of the central lumen where the balloon is inflated can impede fluid flow in the central lumen, and adversely affect an infusion procedure. In addition to reducing flow, a collapsed or blocked catheter tube lumen can reduce cell viability during transport through the lumen by exposing the cells to stress (Note: in some cases, viability has been found to be lowered by around 70-80% when flow is impeded in the central lumen).

In light of the above, it is an object of the present invention to provide an infusion system that can effectively introduce only small groups of particles into a fluid flow. Another object of the present invention is to provide an infusion system that coordinates the flow rate of a particle/fluid medium (i.e. a first fluid) with the flow rate of a fluid (i.e. a second fluid) into which the particle/fluid medium is being introduced. Still another object of the present invention is to provide an infusion system that produces a low exit pressure to reduce the impact on a vessel wall caused when fluid exits a catheter and enters the vessel. It is still another object of the present invention to provide an infusion system having a balloon to regulate blood flow at an infusion site that is not subject to central lumen collapse or blocking during balloon inflation. Yet another object of the present invention is to provide an infusion system that is easy to use, is simple to manufacture and is comparatively cost effective.

SUMMARY OF THE INVENTION

In accordance with the present invention, an infusion system includes an elongated catheter which is formed with a central lumen that extends between the proximal and distal ends of the catheter. Preferably, the catheter is tubular shaped with a smooth, circular, outer surface and, for purposes of description, the catheter defines a longitudinal axis. A source of a fluid medium having particles suspended therein (i.e. a particle/fluid medium) is connected in fluid communication with the proximal end of the catheter, and a separator is connected at the distal end of the catheter. For purposes of the present invention, the separator is provided to prevent the particles from flocculating as they are infused or introduced into a vessel in the vasculature of a patient. As envisioned for the present invention, the particles can be either biologics (i.e. cell, gene or protein) or drugs. And, they can be introduced into the vasculature for intracoronary, intra-arterial, or intravenous therapy.

Structurally, the separator is formed with a plurality of parallel lumens. Thus, with the separator affixed to the distal end of the catheter, each lumen of the separator is individually placed in fluid communication with the central lumen of the catheter. Importantly, each individual lumen is dimensioned to sequentially receive only small groups of particles (i.e. less than ten) therethrough. Specifically, although each lumen can receive several particles at a time, each lumen is sufficiently small to effectively separate particles from clinging to each other as they are received into the lumen. It follows that the system also includes a means for moving the particle/fluid medium through the lumen of the catheter, for further movement of the particles in alignment through individual lumens of the separator. For purposes of the present invention the means for moving this particle/fluid medium can be any such means well known in the pertinent art, such as an IV pole, a syringe, or a pump.

In addition to the separator described above, the system of the present invention also includes a configurable (inflatable) valve, such as a balloon. Specifically, the configurable valve is positioned on the outer surface of the catheter to surround the catheter at a location that is proximal to the separator. Further, the valve is formed with a plurality of apertures that are arranged around the axis of the catheter. The purpose of these apertures is to control the axial movement of a fluid (e.g. blood) past the catheter in a distal direction substantially parallel to the axis of the catheter. This control is preferably provided by an inflator that selectively constricts the apertures of the valve to control the flow rate of fluid through the apertures.

In a preferred embodiment of the present invention, the valve is formed as an annulus that is centered on the axis. With this structure, the annulus has an inner diameter that is affixed to the outer surface of the catheter. The valve also has a substantially non-compliant material positioned on the outer periphery of the annulus that maintains the outer diameter at a predetermined radial distance from the catheter when the valve is inflated into a base configuration. As mentioned previously, the valve can be a balloon as commonly used in the pertinent art, and the balloon can be of any material appropriate for this type of procedure. As examples, the balloon may be nylon, polyethylene, or polyethylene terephthalate (PET). Aside from the non-compliant material, the rest of the annulus is made of a compliant material. Importantly, this compliant material is responsive to the inflator to selectively constrict the apertures. Thus, in operation, an additional inflation of the valve beyond its base configuration substantially maintains the outer diameter at the predetermined radial position, while incrementally constricting the apertures.

Additional features of the present invention include a provision for positioning the catheter in the vasculature over a monorail type guide wire. Also, a fluid flow controller can be provided to meter fluid flow from the source into the central lumen of the catheter at a selected fluid pressure.

Within the context of the present invention, several structural variations are envisioned that will facilitate the infusion of biologics into the vasculature of a patient. These variations can also enhance the diffusion and retention rate of the stem cells, drugs, proteins, or particles by the heart. These include: 1) the creation of a recollection chamber at the distal end of the catheter for establishing a safe and effective fluid infusion velocity for the biologics; 2) the orientation of the proximal (upstream) surface of a separator that will promote separation of biologics from each other prior to their infusion; and 3) an inflatable balloon that will coordinate and control blood flow through the vasculature in cooperation with the infusion of biologics. One additional variation is the use of a venous catheter in place of the catheter disclosed previously.

A recollection chamber used during an intravenous or an arterial infusion is provided at the distal end of the catheter and is created by positioning the separator in the central lumen of the catheter at a distance d from the distal end of the catheter. With this positioning, the recollection chamber will be substantially tubular, it will have a length d, and it will have a diameter the same as that of the central lumen. It should be noted that the valve, or balloon, does not extend to this location near the distal end of the catheter.

Insofar as structural variations of the separator are concerned, in an alternate embodiment of the separator disclosed above, the proximal (upstream) surface is slanted at an angle $\alpha$ relative to the axis of the catheter. Preferably, the angle $\alpha$ will be around 60°, with a consequence that the lumens established by the separator will have different lengths. In one version, the proximal (upstream) surface of the separator will be flat, with the entrance to each lumen angled at the angle $\alpha$ from the axis of the catheter. In another version, this surface will have a stepped configuration so that the entrance to each lumen will be perpendicular to the axis of the catheter. For both versions, the distal (downstream) surface of the catheter will be perpendicular to the axis of the catheter.

In combination, the separator and the recollection chamber function to promote and maintain the separation of biologics as they are being safely infused. In particular, the recollection chamber slows the fluid velocity rate of the infusion fluid, after it has been accelerated through the separator. To further maintain safe fluid flow through the vasculature, an inflatable balloon can be attached to the outer surface of the catheter and it can be selectively inflated to coordinate the respective rates of blood flow and fluid infusion.

In another aspect of the present invention, a reinforcing member is employed to strengthen the catheter wall under the inflatable balloon. With this arrangement, the catheter does not kink or collapse due to the pressure exerted on the catheter wall when the balloon is inflated. Instead, a substantially constant cross-section for the central lumen is maintained during an inflation of the balloon, allowing for the unimpeded flow of particles to pass through the central lumen during an infusion of particles into a patient's vasculature.

In more structural detail, for this embodiment, the reinforcement member is positioned in contact with a section of the catheter wall that encircles a portion of the central lumen. Specifically, the reinforcement member is positioned in contact with the catheter wall under the inflatable balloon.

In one embodiment, the reinforcement member comprises an annular shaped ring that is affixed to the outer surface of the catheter wall under the inflatable balloon. With the annular shaped ring affixed, the ring is oriented substantially perpendicular to a longitudinal axis defined by the infusion catheter and concentric with the axis, to strengthen the catheter wall.

In another embodiment, a separator (as described above) acts as both a filter and the reinforcement member. For this embodiment, the separator is located under the inflatable balloon and positioned in contact with the inner surface of the wall. Thus, the separator provides the dual function of preventing particles from flocculating as they are infused into the vasculature and functions to strengthen the catheter wall to prevent collapse during balloon inflation.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
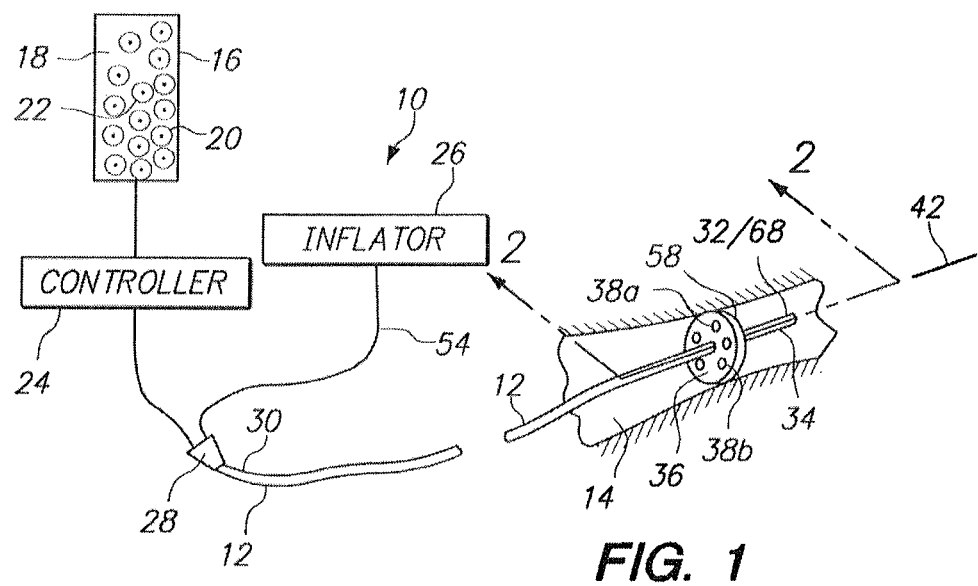
FIG. 1 is a schematic/perspective view of the system of the present invention shown with the system catheter positioned in an operational environment.

Referring initially to FIG. 1 a system for introducing (infusing) a fluid in accordance with the present invention is shown and is generally designated 10. As shown, the system 10 includes a catheter 12 that can be advanced into a vessel 14 to position the catheter 10 at a predetermined location in the vasculature of a patient (not shown). For the purposes of the present invention, the vessel 14 is preferably an artery or a vein in the cardiovascular system of a patient, and the system 10 is used for an intra-arterial, intravenous or intra-coronary protocol.

In detail, FIG. 1 shows that the system 10 includes a source 16 for holding a fluid medium 18. As also shown in FIG. 1, a plurality of particles 20 are suspended in the fluid medium 18 to create a particle/fluid medium 22. For the present invention, the particles 20 may be some form of a drug or, most likely, they will be some form of a biologics (i.e. cell, gene or protein). In any event, the particles 20 will be suspended in the particle/fluid medium 22 for transport from the source 16 through the system 10 and into the vessel 14. As mentioned above for the system 10, the source 16 can be a syringe of a type well known in the pertinent art. FIG. 1 also shows that the system 10 includes a controller 24 that is in fluid communication with the source 16. As envisioned for the present invention, the controller 24 can be any type device that is known in the pertinent art for moving a fluid (e.g. the particle/fluid medium 22) through a fluid flow system (e.g. system 10). In general, such a device may be an IV pump, an IV pole, a syringe, or some other fluid flow metering apparatus. For an embodiment of the system 10 wherein the source 16 is a syringe, however, there is no specific need for a controller 24.

FIG. 1 also shows that the system 10 includes an inflator 26 for a purpose to be discussed below. When both the controller 24 and the inflator 26 are used for the system 10, they can be individually joined at a connector 28 to, respectively, establish separate fluid communication channels with the catheter 12. Preferably, as shown, this connector 28 is connected in fluid communication with the proximal end 30 of the catheter 12.

Still referring to FIG. 1, it is seen that the system 10 includes a tip (filter) 32 (hereinafter sometimes also referred to as a separator 68) that is affixed to the distal end 34 of the catheter 12. Further, it is seen that a valve 36 is mounted on the catheter 12 proximal the distal end 34, and that the valve 36 is formed with a plurality of apertures, of which the apertures 38a and 38b are exemplary. The actual construction of the distal portion of the catheter 12, and the cooperation of structure between the separator 68 and the valve 36 will perhaps be best appreciated with reference to FIG. 2.

Figure 2:
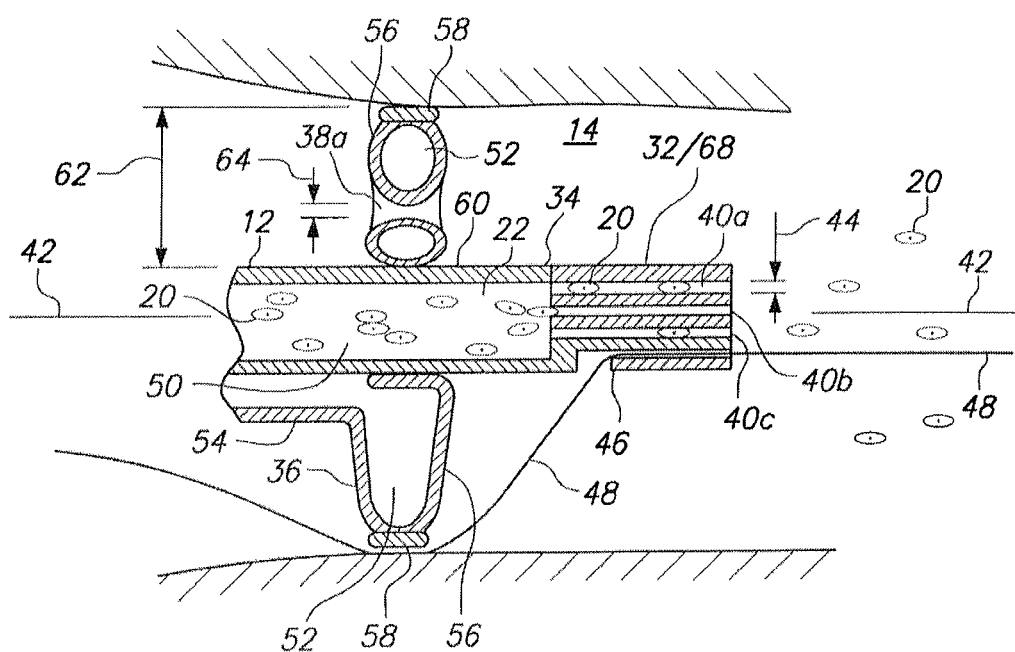
FIG. 2 is a cross-section view of the separator and distal portion of the system catheter as seen along the line 2-2 in FIG. 1.

Referring to FIG. 2, and with specific reference to the separator 68, it will be seen that the separator 68 is formed with a plurality of lumens, of which the lumens 40a, 40b, and 40c are exemplary. More specifically, the lumens extend axially through the separator 68 and are substantially parallel to each other. They are also substantially parallel to the axis 42 that is generally defined by the catheter 12. Importantly, each lumen is established with a diameter 44 that is specifically dimensioned to receive only individual or small groups of particles 20. Although each lumen can receive several de-flocculated particles 20 at a time, the individual particles 20 or small groups of particles remain separated while they transit the lumen (e.g. see lumen 40a). Further, the separator 68 can be formed with a monorail lumen 46 that will interact with a guide wire 48, in a manner well known by the skilled artisan, for the purpose of positioning the catheter 12 within the vessel 14.

With the structure of the separator 68 in mind, as described above, it is an important aspect of the present invention that the diameter 44 of each lumen be dimensioned to prevent the entry of large groups of flocculated particles 20 into the lumen from the central lumen 50 of the catheter 12. In particular, for different therapeutic protocols, it may be very necessary that the particles 20 be dispersed as they enter the vessel 14, to thereby minimize the possibility of subsequent flocculation in the vessel 14, which may lead to heart attack or stroke if the cells are infused into the coronary circulatory system. Further, dispersion of the particles 20 as they enter the vessel 14 will provide better mixing with the blood for more efficient distribution to tissue.

Recall, the valve 36 is formed with a plurality of apertures. Further, with cross reference to FIG. 1 and FIG. 2, it will also be appreciated that, when inflated, the valve 36 is generally shaped as an annulus and is formed with an inflation chamber 52. As shown, the inflation chamber 52 is connected in fluid communication with the inflator 26 via an inflation line 54. Within this structure, the inflation line 54 can be integrated into the catheter 12. For operational purposes, the valve 36 includes a valve body 56 that is made of a compliant, inflatable material. The valve 36 also includes a rim 58 made of a substantially non-compliant material that is located on the periphery of the annulus shaped valve 36. For the system 10, the valve 36 is located proximal to the separator 68, and it is affixed to the outer surface 60 of the catheter 12 by any means known in the pertinent art, such as by gluing or bonding.

Operationally, the valve 36 (balloon) starts from a deflated configuration, and it is then inflated by the inflator 26 into a base configuration (see FIGS. 1 and 2) wherein the valve 36 is constrained by the rim 58. In this base configuration, the valve 36 will extend from the surface 60 of catheter 12 through a radial distance 62 and, in the base configuration, it will most likely make contact with the vessel 14. Also, in the base configuration, each aperture (e.g. aperture 38a) will have a diameter 64. With an additional inflation of the valve 36 by the inflator 26, however, two different structural consequences occur. For one, the rim 58 does not expand from the base configuration. Thus, the radial distance 62 remains substantially constant. For another, the valve body 56 will expand in response to the inflator 26 such that the apertures are incrementally constricted. Stated differently, and with specific reference to the aperture 38a, the diameter 64 will be diminished. In an alternate embodiment for the present invention, there may be no need for the valve 36.

For an operation of the system 10 in an intra-arterial, intravenous or intracoronary protocol, a guide wire 48 is first prepositioned in the vasculature of a patient. The guide wire 48 is then received into the monorail lumen 46 of the catheter 12, and the catheter 12 is advanced over the guide wire 48 and into position in the vasculature of the patient. Once the catheter 12 has been properly positioned, the valve 36 is inflated into its base configuration, or beyond. The exact extent of inflation for valve 36 will depend on the desired flow rate for fluid through the apertures in the vessel 14. With the valve 36 inflated, the controller 24 is then activated to cause a flow of particle/fluid medium 22 from the source 16 and through the central lumen 50 of the catheter 12. As particles 20 in the particle/fluid medium 22 arrive at the separator 68, the respective diameters 44 of individual lumens in the separator 68 allow only individual particles 20 or small groups of particles 20 to enter the lumen. Thus, the flocculation of particles 20 in the central lumen 50 is disrupted, and flocculation of the particles 20 after they have passed through the separator 68 is minimized. Although the above discussion has focused on applications of the system 10 within the cardiovascular system of a patient, the system 10 is appropriate for any use wherein particles 20 may be suspended in a particle/fluid medium 22 for subsequent release as individual particle 20 into a fluid flow (e.g. blood flow through a vessel 14).

Figure 3:
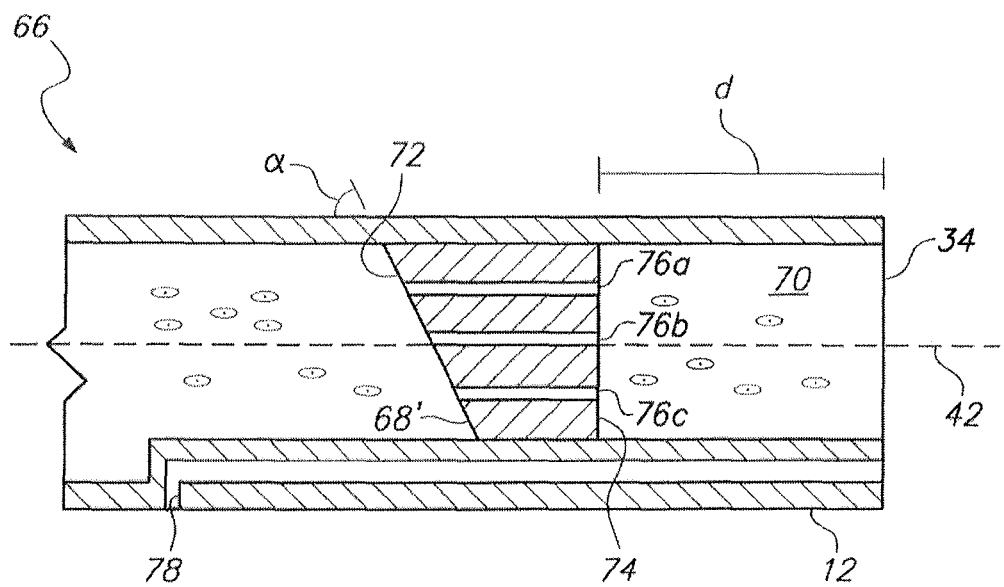
FIG. 3 is a cross-section view of an alternate embodiment of the infusion tip as seen along line 2-2 in FIG. 1.

Referring to FIG. 3, an infusion tip for biologics is shown and generally is designated 66. In this embodiment, a separator 68' is located in the central lumen 50 of the catheter 12 at a distance d from the distal end 34 of the catheter 12. As so located, the separator 68' creates a recollection chamber 70 having a length d at the distal end 34 of the catheter 12. Specifically, the recollection chamber 70 is a tubular section formed onto the distal end 34 of the catheter 12. If necessary, the recollection chamber 70 may be established by a stand-alone piece of tubing that can be attached to the distal end 34 of the catheter 12.

Still referring to FIG. 3, it is seen that the separator 68' has a proximal (upstream) surface 72 and a distal (downstream) surface 74. In detail, the proximal surface 72 of the separator 68' is oriented at a slant angle α relative to the axis 42 of the catheter 12. The distal surface 74 of the separator 68', however, is perpendicular to the axis 42, and it is substantially flat. Keeping in mind the structure disclosed above, a consequence of the slanted proximal surface 72 is that the proximal end of each lumen 76a-c will also be slanted at angle α relative to the axis 42 of catheter 12. Consequently, when fluid flows through the catheter 12 and encounters the slanted proximal surface 72 of the catheter 12, it is redirected to flow through the lumens 76a-c of the separator 68'. In operation, this redirection helps prevent particles 20 in the fluid from flocculating prior to entering the vasculature of the patient. Upon exiting the lumens 76a-c of the separator 68', the fluid enters the recollection chamber 70 where it is allowed to slow down before entering the vasculature of the patient.

Figure 4:
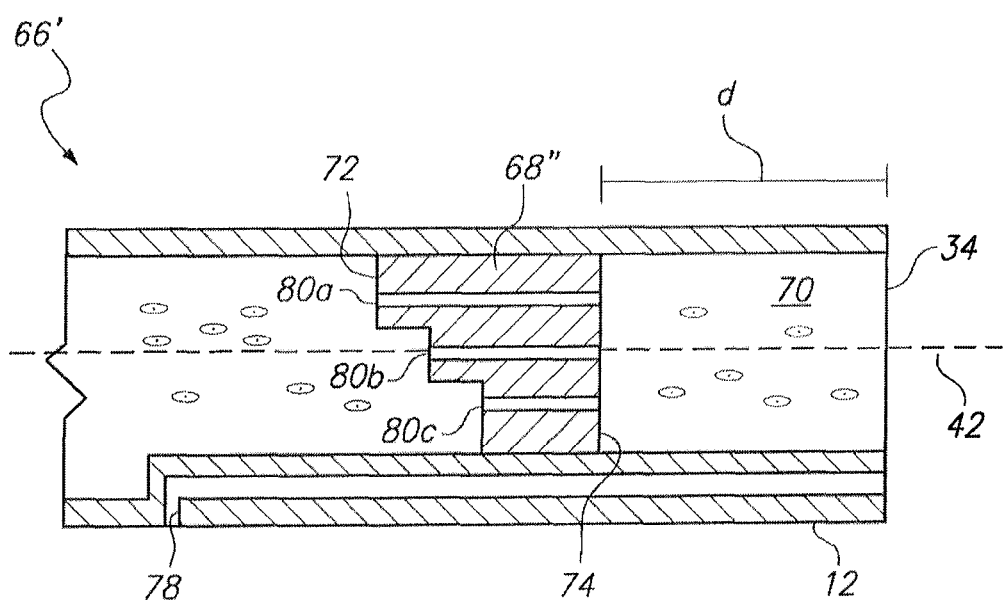
FIG. 4 is a cross-section view of an alternate embodiment of the infusion tip shown in FIG. 3.

For embodiments shown in FIGS. 3 and 4, the guide wire exit lumen 78 is formed onto the catheter 12 at a location approximately 25-30 millimeters proximal the separator 68' and 68".

Referring now to FIG. 4, a variation of the infusion tip 66' is shown wherein the proximal surface 72 of the separator 68" is formed with a step configuration. Due to the step configuration, the proximal end of each lumen 80a-c remains substantially perpendicular to the axis 42 of the catheter 12. Thus, in all important respects, the infusion tips 66, 66' shown in FIGS. 3 and 4, respectively, are the same with the exception that the proximal surfaces differ. It should be noted that the proximal surface 72 of the separator 68 can also take the shape shown in FIG. 2 for the separator 32/68.

Figure 5A:
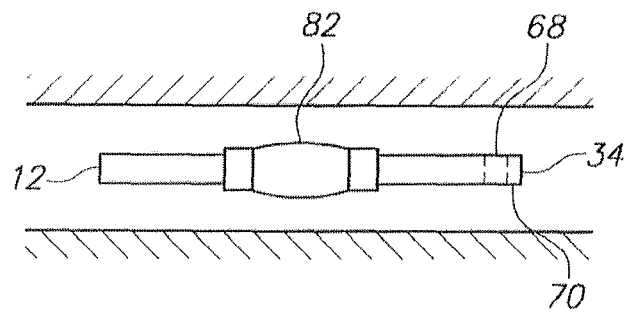
FIG. 5A is a plan view of the balloon of the present invention in a deflated configuration and shown with the catheter positioned in an operational environment.
Figure 5B:
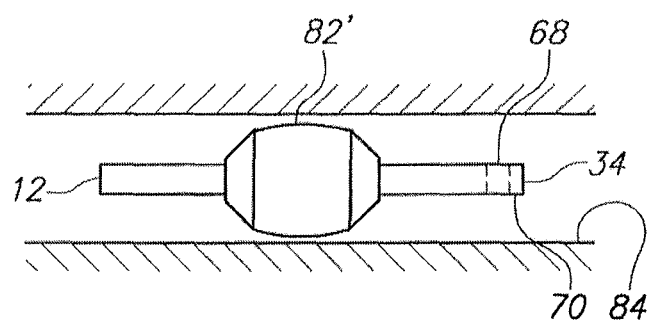
FIG. 5B is a plan view of the balloon of the present invention in an inflated configuration and shown with the system catheter positioned in an operational environment.

Referring now to FIG. 5A and FIG. 5B, a selectively inflatable balloon 82 is shown attached to the catheter 12 at a location proximal the separator 68. When inflated as shown in FIG. 5B, the balloon 82' controls the flow rate of blood around the catheter 12 by expanding radially away from the catheter 12 towards the vessel wall 84. As envisioned for the present invention, the flow rate of the blood outside the catheter 12 should be compatible with the flow rate of fluid inside the catheter 12 in order to minimize turbulence at the distal end 34 of the catheter 12. In any event, the overall objective for the recollection chamber 70 and the inflatable balloon 82 is to decrease the probability of damage or injury to the vasculature of the patient during an infusion by decreasing the flow rate of blood to allow particles additional time to diffuse and to travel through blood vessels and into the tissue to be treated.

Figure 6:
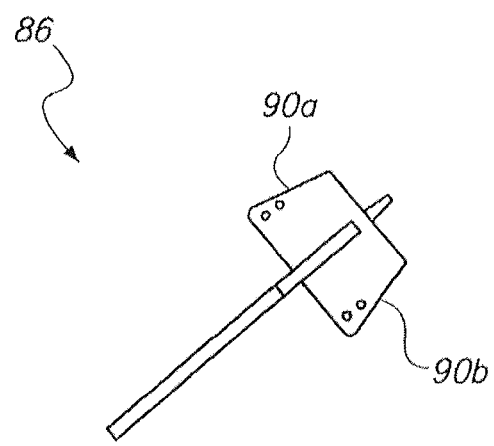
FIG. 6 is a plan view of the venous catheter for the present invention.

Referring now to FIG. 6, it is to be appreciated that an infusion tip 66 in accordance with the present invention can be employed in a venous catheter 86 of a type that is well-known in the pertinent art. If a venous catheter 86 is used, the infusion tip 66 will be essentially the same as disclosed above for other embodiments. The advantage here is that, in appropriate situations, the venous catheter 86 may be secured to the patient prior to the release of fluid from the fluid source 16. For example, the wings 90a-b are secured to the patient prior to the release of fluid 18 from the fluid source 16. In all other important respects, the operation of the venous catheter 86 with the infusion tip 66 of the present invention is identical to the operation disclosed previously.

Figure 7:
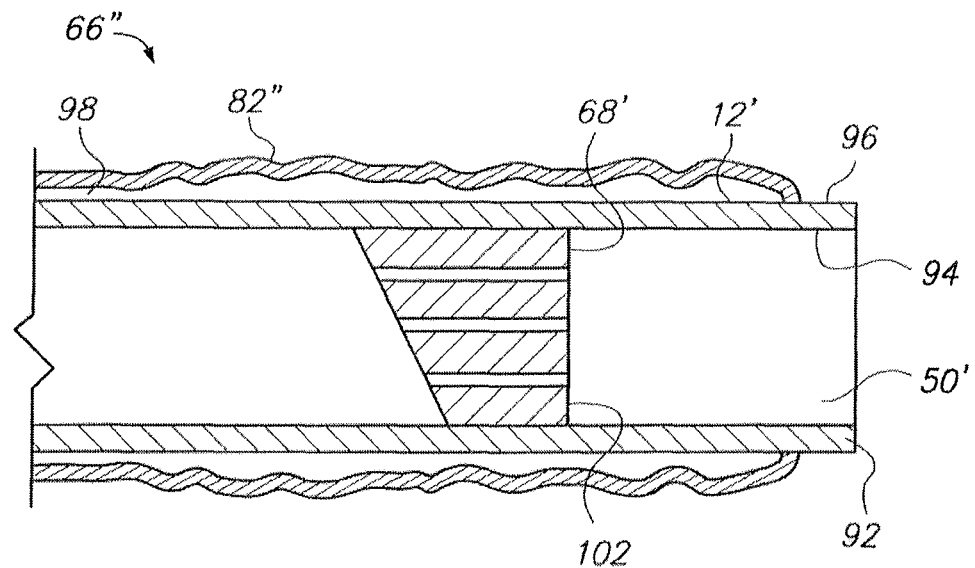
FIG. 7 is a cross-section view of an alternate embodiment of an infusion tip as seen along line 2-2 in FIG. 1, having a balloon for regulating/controlling the axial movement of a fluid (e.g. blood) past the catheter and a separator which also functions to prevent catheter tube collapse during balloon inflation, shown with the balloon in a deflated state.

FIG. 7 shows another embodiment of an infusion tip 66" having an elongated catheter 12' having a tubular-shaped wall 92 with an inner surface 94 and an outer surface 96. As shown, the inner surface 94 of the wall 92 surrounds a central lumen 50' for the catheter 12'. FIG. 7 also shows that an inflatable balloon 82" is mounted on the outer wall 96. An inflation lumen 98 is provided to selectively inflate the balloon 82" (inflated balloon 82" shown in FIG. 8). It can be seen that a portion of the outer wall 96 cooperates with the balloon 82" to establish an inflation chamber 100. To inflate the balloon 82", an inflation fluid is pumped through the inflation lumen 98, for example using the inflator 26 shown in FIG. 1 and described above, to establish a preselected inflation pressure in the inflation chamber 100. It is to be appreciated that this pressure will establish a force on the wall 92 that is directed radially inward and tends to constrict or collapse the catheter 12'. As indicated above, collapse or constriction of the catheter 12' can undesirably impede flow in the central lumen and/or stress cells such as stem cells in the central lumen flow lowering cell viability (sometimes by as much as 70-80%).

To prevent this collapse, FIG. 7 shows that the infusion tip 66" can include a reinforcing member 102 to support the catheter wall 92 under the inflatable balloon 82". As shown, for the FIG. 7 embodiment, the reinforcing member 102 is a separator 68' (as described above with reference to FIG. 3) that is positioned in the central lumen 50' under the balloon 82". Alternatively, the separator 32/68 shown in FIG. 2, the separator 68" shown in FIG. 4 or a similar separator may be positioned in the central lumen 50' under the balloon 82" to reinforce the wall 92 during inflation of the balloon 82". Functionally, the reinforcing member 102 prevents collapse of the wall 92 and maintains a substantially constant cross-section for the central lumen 50' during an inflation of the balloon 82", allowing for unimpeded fluid flow to pass through the central lumen 50' during an infusion.

Figure 8:
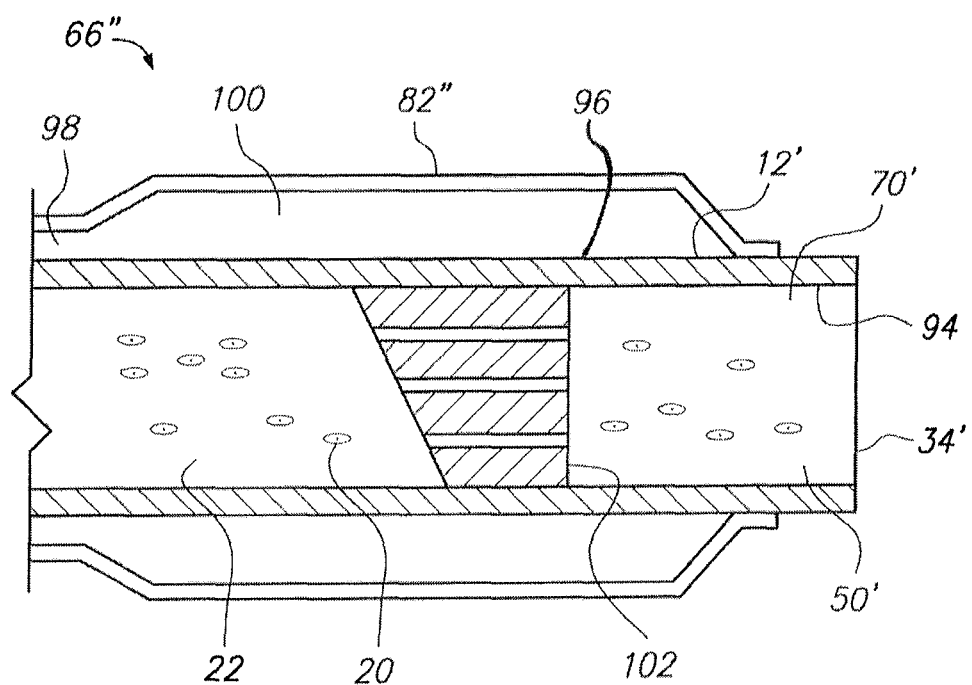
FIG. 8 is a cross-section view of the infusion tip shown in FIG. 7, shown with the balloon in an inflated state.

With the arrangement shown in FIGS. 7 and 8, the infusion tip 66" can be advanced to a treatment site suitable for delivery of particles 20 with the balloon 82" in a deflated state (as shown in FIG. 7). Next, with the infusion tip 66" at the treatment site, the balloon 82" is selectively inflated (as shown in FIG. 8) to control and/or regulate the flow of blood in the vasculature for blood flowing past the infusion tip 66". Once the blood flow (not shown) has been adequately regulated, a particle/fluid medium 22 including particles 20 can be introduced into the central lumen 50' and passed through the separator 68' to prevent large, flocculated particles from entering the bloodstream. The particle/fluid medium 22 then passes through a recollection chamber 70' and exits the distal end 34' of the catheter 12'. After the infusion, the balloon 82" can be deflated and the infusion tip 66" withdrawn from the patient's vasculature.

Figure 9:
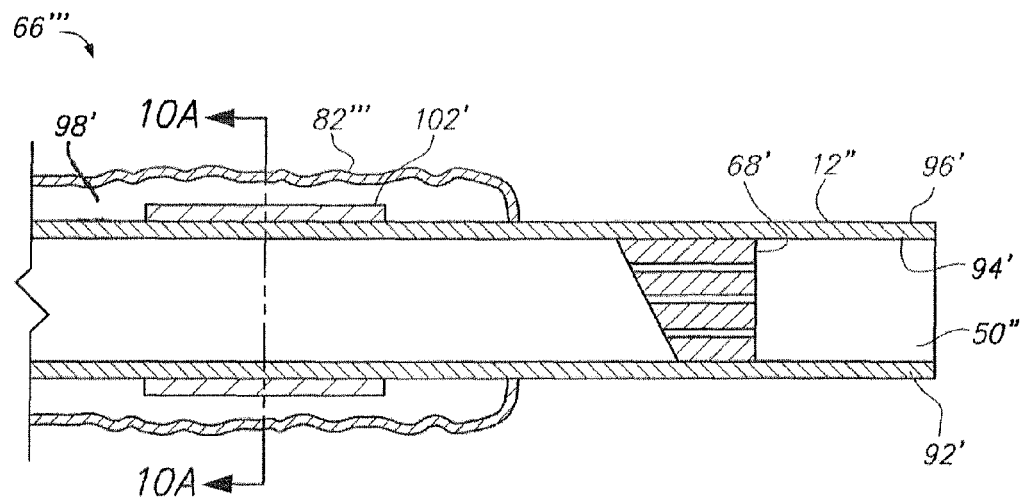
FIG. 9 is a cross-section view of an alternate embodiment of an infusion tip as seen along line 2-2 in FIG. 1, having a balloon for regulating/controlling the axial movement of a fluid (e.g. blood) past the catheter and an annular shaped ring to prevent catheter tube collapse during balloon inflation, shown with the balloon in a deflated state.
Figure 10:
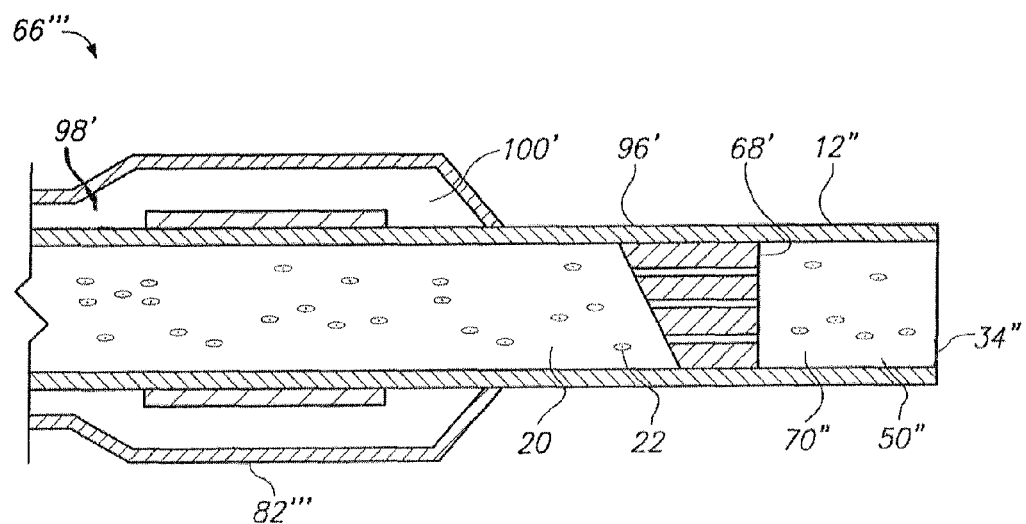
FIG. 10 is a cross-section view of the infusion tip shown in FIG. 9, shown with the balloon in an inflated state.
Figure 10A:
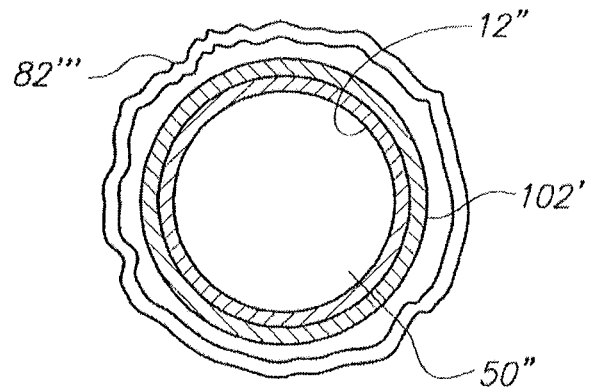
FIG. 10A is a cross-section view of the infusion tip embodiment shown in FIG. 9, as seen along line 10A-10A.

FIGS. 9, 10 and 10A show another embodiment of an infusion tip 66''' for an elongated catheter 12" having a tubular-shaped wall 92' (see FIG. 9) with an inner surface 94' and an outer surface 96'. As shown, the inner surface 94' of the wall 92' surrounds a central lumen 50" for the catheter 12". FIG. 7 also shows that an inflatable balloon 82''' is mounted on the outer wall 96'. An inflation lumen 98' is provided to selectively inflate the balloon 82''' (inflated balloon 82''' shown in FIG. 10). It can be seen that a portion of the outer wall 96' cooperates with the balloon 82''' to establish an inflation chamber 100'. To inflate the balloon 82''', an inflation fluid is pumped through the inflation lumen 98', for example using the inflator 26 shown in FIG. 1 and described above, to establish a preselected inflation pressure in the inflation chamber 100'. It is to be appreciated that this pressure will establish a force on the wall 92' that is directed radially inward and tends to constrict or collapse the catheter 12". As indicated above, collapse or constriction of the catheter 12" can undesirably impede flow in the central lumen and/or stress cells such as stem cells in the central lumen flow lowering cell viability (sometimes by as much as 70-80%).

To prevent this collapse, FIG. 9 shows that the infusion tip 66''' can include a reinforcing member 102' to support the catheter wall 92' under the inflatable balloon 82'''. As shown, for the FIG. 9 embodiment, the reinforcing member 102' can be formed as an annular shaped ring that is affixed to the outer surface 96' of the catheter wall 94' under the balloon 82'''. Once affixed, the ring shaped reinforcing member 102' is oriented substantially perpendicular to a longitudinal axis 42' defined by the infusion catheter 12", as shown. Functionally, the reinforcing member 102' prevents collapse of the wall 92' and maintains a substantially constant cross-section for the central lumen 50" during an inflation of the balloon 82''', allowing for unimpeded fluid flow to pass through the central lumen 50" during an infusion.

With the arrangement shown in FIGS. 9 and 10, the infusion tip 66''' can be advanced to a treatment site suitable for delivery of particles 20 with the balloon 82''' in a deflated state (as shown in FIG. 9). Next, with the infusion tip 66''' at the treatment site, the balloon 82''' is selectively inflated (as shown in FIG. 10) to control and/or regulate the flow of blood in the vasculature for blood flowing past the infusion tip 66'''. Once the blood flow (not shown) has been adequately regulated, a particle/fluid medium 22 including particles 20 can be introduced into the central lumen 50" and passed through the separator 68' to prevent large, flocculated particles from entering the bloodstream. Alternatively, the separator 32/68 shown in FIG. 2, the separator 68" shown in FIG. 4, or a similar separator may be used. The particle/fluid medium 22 then passes through a recollection chamber 70" and exits the distal end 34" of the catheter 12". After the infusion, the balloon 82''' can be deflated and the infusion tip 66''' withdrawn from the patient's vasculature.

Figure 10B:
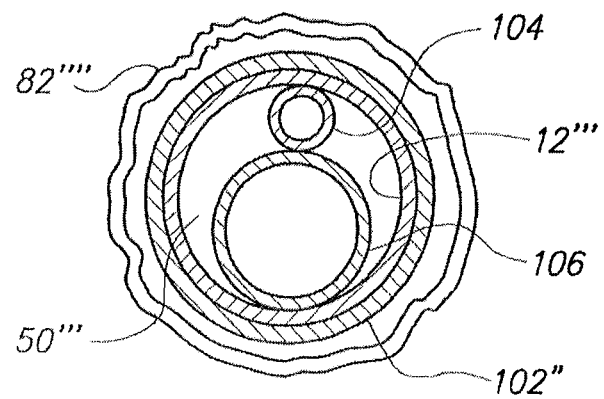
FIG. 10B is a cross-section view as in FIG. 10A showing another infusion tip embodiment having an inflation tube and infusion tube within the central lumen of the catheter.

FIG. 10B shows another infusion tip embodiment having an inflation tube 104 and an infusion tube 106 positioned within the central lumen 50''' of the catheter 12'''. For this embodiment, an inflatable balloon 82'''' is mounted on the catheter 12''', and is connected in fluid communication with the inflatable balloon 82''''. To prevent a collapse of the catheter 12''' during inflation of the balloon 82'''', a reinforcing member 102" is provided to support the catheter 12'''. Collapse of the catheter 12''' during inflation may constrict the infusion tube 106 and undesirably impede flow in the infusion tube 106 and/or stress cells, such as stem cells in the infusion tube 106, lowering cell viability. As shown, for the FIG. 10B embodiment, the reinforcing member 102" can be formed as an annular shaped ring that is affixed to the outer surface of the catheter 12''' under the balloon 82''''.

While the particular Infusion Catheter Tip for Biologics with Reinforced External Balloon Valve as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for infusing stem cells into a patient at a predetermined site in the vasculature, which comprises:
   an elongated catheter having a tubular-shaped wall with an inner surface and an outer surface, wherein the inner surface of the wall defines a central lumen extending between a proximal end and a distal end of the catheter;
   an inflatable balloon mounted on the outer surface of the catheter wall;

an inflator connected in fluid communication with the balloon for selectively inflating the balloon to control and regulate the flow of blood in the vasculature past the catheter;

a reinforcement member positioned in contact with a section of the catheter wall encircling a portion of the central lumen, wherein the reinforcement member is positioned under the inflatable balloon, to strengthen the catheter wall and to maintain a substantially constant cross-section for the central lumen during an inflation of the balloon; and a separator positioned distal of the inflatable balloon and defining a plurality of lumens in fluid communication with the central lumen;

wherein the plurality of lumens of the separator are arranged to receive groups of cells traveling through the central lumen of the elongated catheter and to separate the groups of cells into smaller groupings or individual cells, allowing the smaller groupings or individual cells to pass through the separator and away from the distal end of the elongated catheter.

2. A system as recited in claim 1 wherein the infusion catheter defines a longitudinal axis, and wherein the reinforcement member comprises at least one annular shaped ring, with the ring affixed to the outer surface of the catheter wall and oriented substantially perpendicular to the longitudinal axis.

3. A system as recited in claim 1 further comprising:

a source of a fluid medium having stem cells suspended therein, wherein the source is connected in fluid communication with the proximal end of the catheter.

4. A system as recited in claim 3 wherein:

the separator has a proximal end and a distal end formed with the plurality of lumens extending therebetween, wherein the separator is positioned in the lumen of the catheter at a distance d from the distal end thereof to establish a recollection chamber at the distal end, and to individually place each lumen of the separator in fluid communication with the central lumen, and wherein each individual lumen is dimensioned to sequentially receive stem cells therethrough.

5. A system as recited in claim 4 further comprising:

an infusion device for moving the fluid medium with suspended particles through the lumen of the catheter, for further movement of the particles in a separated alignment through individual lumens of the separator for reconstitution of the fluid medium with stem cells in the recollection chamber.

6. A system as recited in claim 5 wherein the catheter defines an axis and the proximal end of the separator is slanted at an angle α relative to the axis, with the distal end of the separator being substantially perpendicular to the axis.

7. A system as recited in claim 5 wherein the proximal end of each lumen in the separator is oriented substantially perpendicular to the axis of the separator to establish a step configuration for the proximal end of the separator.

8. A system for introducing particles into the vasculature of a patient, the system comprising:

an elongated catheter formed with a central lumen extending between a proximal end and a distal end, wherein the catheter defines an axis;

a source of the particles suspended in a fluid, wherein the source is connected in fluid communication with the proximal end of the catheter;

a substantially cylindrical shaped separator in fluid communication with the particle source, wherein the separator has a proximal end and a distal end and is formed with a plurality of longitudinally aligned, parallel lumens, with each lumen dimensioned to receive particles therethrough;

an inflatable balloon positioned around the catheter and affixed thereto, with the balloon extendable in a radial direction outward from the catheter to control blood flow around the catheter in a direction substantially parallel to the axis;

a reinforcement member positioned in contact with a section of the catheter wall encircling a portion of the central lumen, wherein the reinforcement member is positioned under the inflatable balloon, to strengthen the catheter wall and to maintain a substantially constant cross section for the central lumen during an inflation of the balloon;

an infusion device for moving particles from the source, through the separator, and into the vasculature of the patient; and an inflator for selectively configuring the balloon from a base configuration to a secondary configuration, wherein the balloon is deflated in the base configuration and inflated in the secondary configuration;

wherein the balloon is positioned around the catheter at a location proximal the separator.

9. A system as recited in claim 8 wherein the reinforcement member comprises at least one annular shaped ring, with the ring affixed to the outer surface of the catheter wall and oriented substantially perpendicular to the longitudinal axis.

10. A system as recited in claim 8 wherein the separator is positioned in the catheter at a distance d from the distal end thereof to establish a recollection chamber between the separator and the distal end of the catheter.

11. A system as recited in claim 8 wherein the proximal end of the separator is slanted at an angle α relative to the axis, with the distal end of the separator being substantially perpendicular to the axis.

12. A system as recited in claim 8 wherein the proximal end of each lumen in the separator is oriented substantially perpendicular to the axis of the catheter to establish a step configuration for the proximal end of the separator.

13. A system as recited in claim 8 wherein the particles are selected from a group consisting of agents useful for gene therapy, drug therapy and protein therapy.

14. A system as recited in claim 8 wherein the particles are stem cells.

15. A method for introducing particles into the vasculature of a patient, the method comprising the steps of:

providing an elongated catheter having a tubular-shaped wall with an inner surface and an outer surface, wherein the inner surface of the wall defines a central lumen extending between a proximal end and a distal end of the catheter, wherein an inflatable balloon is mounted on the outer surface of the catheter wall, wherein a reinforcement member is positioned in contact with a section of the catheter wall encircling a portion of the central lumen, wherein the reinforcement member is positioned under the inflatable balloon to strengthen the catheter wall and to maintain a substantially constant cross section for the central lumen during an inflation of the balloon, and wherein a separator defining a plurality of lumens in fluid communication with the central lumen is positioned distal of the inflatable balloon;

connecting an inflator in fluid communication with the balloon;

selectively inflating the balloon to control and regulate the flow of blood in the vasculature past the catheter; and using an infusion device to move particles from a source, through the central lumen, through the separator, and into the vasculature of the patient;

wherein the plurality of lumens of the separator are arranged to receive groups of cells traveling through the central lumen of the elongated catheter and to separate the groups of cells into smaller groupings or individual cells, allowing the smaller groupings or individual cells to pass through the separator and away from the distal end of the elongated catheter.

16. A method as recited in claim 15 wherein the step of using an infusion device to move particles from a source, through the central lumen, and into the vasculature of the patient is performed with the balloon in an inflated state.

17. An infusion system for infusing cells into a patient, comprising:

an elongated catheter having a proximal end and distal end and a central lumen extending between the proximal end and the distal end, the distal end of the elongated catheter arranged for insertion into a patient;

a separator at the distal end of the elongated catheter, the separator defining a plurality of lumens in fluid communication with the central lumen; and an expandable member positioned along an exterior surface of the elongated catheter and expandable from a contracted configuration to an expanded configuration;

wherein the plurality of lumens of the separator are arranged to receive groups of cells traveling through the central lumen from the proximal end to the distal end of the elongated catheter and to separate the groups of cells into smaller groupings or individual cells, allowing the smaller groupings or individual cells to pass through the separator and away from the distal end of the elongated catheter; and wherein the infusion system is arranged so that all cells infused into the patient from the central lumen pass through the separator; and wherein the expandable member is positioned proximal of the separator.

18. The infusion system of claim 17, comprising a guide wire lumen extending alongside said plurality of lumens of said separator.

19. The infusion system of claim 17, comprising a source of fluid medium having cells suspended therein, wherein the source of fluid medium is connected in fluid communication with the proximal end of the elongated catheter and the central lumen; and wherein the plurality of lumens of the separator are arranged to de-flocculate cells received from the source of fluid medium into smaller groupings or individual cells, allowing the smaller groupings or individual cells to pass through the separator and away from the distal end for the elongated catheter.

20. The infusion system of claim 19, comprising a device for moving the fluid medium having cells suspending therein through the central lumen of the elongated catheter and the plurality of lumens of the separator.

21. The infusion system of claim 17, wherein the expandable member is an inflatable balloon.

22. The infusion system of claim 21, comprising an inflator for selectively expanding or contacting the inflatable balloon.

23. The infusion system of claim 17, wherein the separator is affixed to the distal end of the elongated catheter.

24. An infusion system for infusing cells into a patient, comprising:

an elongated catheter having a proximal end and distal end and a central lumen extending between the proximal end and the distal end, the distal end of the elongated catheter arranged for insertion into a patient;

a separator at the distal end of the elongated catheter, the separator defining a plurality of lumens in fluid communication with the central lumen; and an expandable member positioned along an exterior surface of the elongated catheter and expandable from a contracted configuration to an expanded configuration;

wherein the plurality of lumens of the separator are arranged to receive groups of cells traveling through the central lumen from the proximal end to the distal end of the elongated catheter and to separate the groups of cells into smaller groupings or individual cells, allowing the smaller groupings or individual cells to pass through the separator and away from the distal end of the elongated catheter; and wherein the infusion system is arranged so that all cells infused into the patient from the central lumen pass through the separator; and wherein a length of the infusion system extending from the expandable member to a distal end of the infusion system includes the separator and is free of another expandable member.

25. The infusion system of claim 24, comprising a guide wire lumen extending alongside said plurality of lumens of said separator.

26. The infusion system of claim 25, comprising a source of fluid medium having cells suspended therein, wherein the source of fluid medium is connected in fluid communication with the proximal end of the elongated catheter and the central lumen; and wherein the plurality of lumens of the separator are arranged to de-flocculate cells received from the source of fluid medium into smaller groupings or individual cells, allowing the smaller groupings or individual cells to pass through the separator and away from the distal end for the elongated catheter.

27. The infusion system of claim 26, comprising a device for moving the fluid medium having cells suspending therein through the central lumen of the elongated catheter and the plurality of lumens of the separator.

28. The infusion system of claim 27, wherein the expandable member is an inflatable balloon.

29. The infusion system of claim 28, comprising an inflator for selectively expanding or contacting the inflatable balloon.

* * * * *